United States Patent [19]
van der Bruggen et al.

[11] Patent Number: 5,629,166
[45] Date of Patent: May 13, 1997

[54] METHOD FOR IDENTIFYING INDIVIDUALS SUFFERING FROM A CELLULAR ABNORMALITY SOME OF WHOSE ABNORMAL CELLS PRESENT COMPLEXES OF HLA-C-CLONE 10/MAGE-1 DERIVED PEPTIDES, AND METHODS FOR TREATING SAID INDIVIDUALS

[75] Inventors: Pierre van der Bruggen; Thierry Boon-Falleur, both of Brussels, Belgium

[73] Assignee: Ludwig Institute for Cancer Research, New York, N.Y.

[21] Appl. No.: 288,977

[22] Filed: Aug. 11, 1994

Related U.S. Application Data

[63] Continuation of Ser. No. 8,446, Jan. 22, 1993, abandoned.
[51] Int. Cl.$^6$ ................................................. G01N 33/574
[52] U.S. Cl. ........................... 435/7.23; 435/7.21; 435/6; 436/64
[58] Field of Search ................................. 424/93.1, 93.7, 424/93.71; 435/240.2, 7.23, 7.21, 6; 436/64

[56] References Cited

FOREIGN PATENT DOCUMENTS

WO9220356  11/1992  WIPO .

OTHER PUBLICATIONS van der Bruggen et al., "A Gene Encoding An Antigen Recognized by Cytolytic T Lymphocytes on a Human Melanoma", Sci. 254: 1643–1647 (Dec. 13, 1991).
Sibille et al., "Structure of the Gene of Tum– Transplantation Antigen P198: A Point Mutation Generates a New Antigenic Peptide", J. Exp. Med. 172: 35–45 (Jul., 1990).
Szikora et al., "Structure of the gene of Tum– transplantation antigen P35B: presence of a point mutation in the antigenic allele", EMBO J 9(4): 1041–1050 (1990).
Van den Eynde et al., "Presence on a Human Melanoma of Multiple Antigens Recognized by Autologous CTL", Int. J. Cancer 44: 634–640 (1989).
Lurquin et al., "Studies of the Gene of Tum–Transplantation Antigen P91A: The Mutated Exon Encodes a Peptide Recognized with $L^d$ by Cytolytic T Cells", Cell 58: 293–305 (Jul. 28, 1989).
Wolfel et al., "Immunogenic tum– variants obtained by mutagenesis of mouse mastocytoma P815", Immunogenetics 26: 178–187 (1987).
Boon et al., "Genes Coding for Tum– Transplantation Antigens a Model for TSTA" in Immunology, vol. VII (Springer Verlag, 1989), pp. 1063–1070.
DePlaen et al., "Immunogenic tum– variants of mouse tumor P815: Cloning of the gene of tum– antigen P91A and identification of the tum– mutation", Proc. Natl. Acad. Sci. USA 85: 2274–2278 (Apr. 1988).
Boon et al., "Immunogenic Variants Obtained by Mutagenesis of Mouse Mastocytoma P815", J. Exp. Med. 152: 1184–1193 (Nov. 1990).
Greenberg, "Therapeutic of Murine Leukemia With Cyclophosphamide and Immune LYT $2^+$ Cells: Cytolytic T Cells Can Mediate Eradication of Disseminated Leukemia", J. Immunol. 135(5): 1917–1922 (Mar. 1986).
Kast et al., "Eradication of Adenovirus El–Induced Tumors by EIA–specific Cytotoxic T Lymphocytes", Cell 59: 603–614 (Nov. 17, 1989).
Lynch et al., "Immunotherapeutic elimination of syngeneic tumors in vitro by Cytotoxic T Lymphocytes generated in vitro from lymphocytes from the draining lymph nodes of tumor bearing mice", Eur. J. Immunol. 21: 1403–1410 (1991).
Riddell et al., "Restoration of Viral Immunity In Immunodeficient Humans By The Adoptive Transfer of T Cell Clones", Science 257: 238–241 (Jul. 10, 1992).
Melief, et al.; Cancer Surveys, vol. 13, pp. 81–99; 1992.
De Plaen et al (1994) Immunogenetics 40 : 360–369.
Koriyone et al (1990) J. Immunol. 145(11) : 3714–3718.
van der Bruggen et al (1994) Eur. J. Immunol. 24 : 2134–2140.
Chen et al (1994) Proc. Nat'l. Acad. Sci. 91 : 1004–1008.
Traversari et al (1992) Immunogenetics 35 : 145–152.
Traversari et al (1992) J. Exp. Med. 176 : 1453–1457.
Hay et al (eds.) "American Type Culture Collection Catalog of Cell Lines and Hybridomas, Seventh Edition, 1992", ATCC, Rockville, Md., p. 158.

Primary Examiner—Toni R. Scheiner
Attorney, Agent, or Firm—Felfe & Lynch

[57] ABSTRACT

The invention relates to the identification of complexes of HLA-C-clone 10 and MAGE-1 derived peptides on the surfaces of abnormal cells. The therapeutic and diagnostic ramifications of this observation are the subject of the invention.

7 Claims, 1 Drawing Sheet

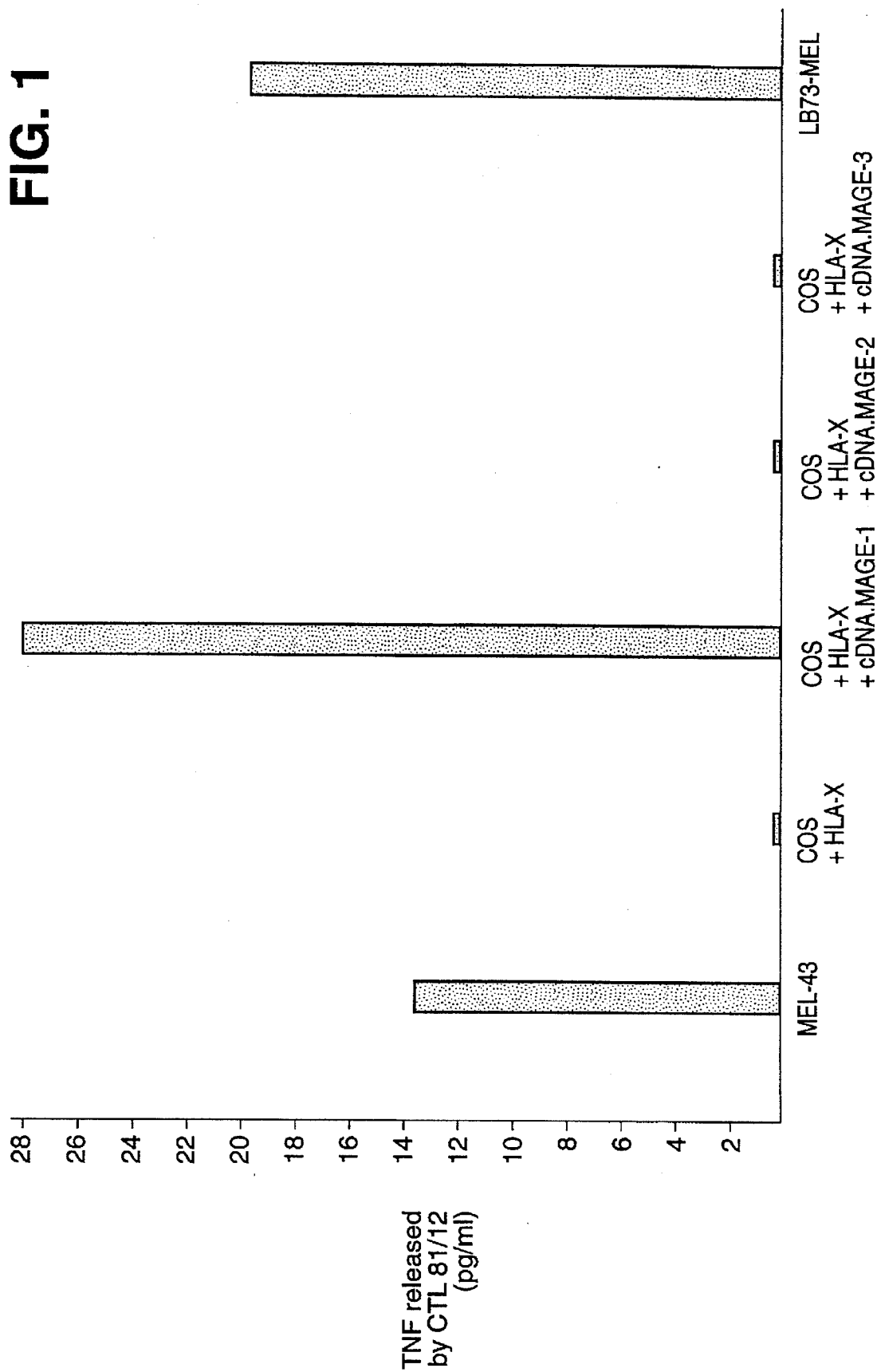

METHOD FOR IDENTIFYING INDIVIDUALS SUFFERING FROM A CELLULAR ABNORMALITY SOME OF WHOSE ABNORMAL CELLS PRESENT COMPLEXES OF HLA-C-CLONE 10/MAGE-1 DERIVED PEPTIDES, AND METHODS FOR TREATING SAID INDIVIDUALS

This application is a continuation of application Ser. No. 08/008,446, filed Jan. 22, 1993, now abandoned.

FIELD OF THE INVENTION

This invention relates to various therapeutic methodologies derived from the recognition that certain abnormal cells present complexes of HLA-C-clone 10 and peptides derived from a molecule referred to as MAGE-1 on their surfaces. In addition, it relates to the ability to identify those individuals diagnosed with conditions characterized by cellular abnormalities whose abnormal cells present this complex.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard see Male et al., *Advanced Immunology* (J. P. Lipincott Company, 1987), especially chapters 6–10. The interaction of T cell and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Recently, much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, as WO92/20356 and incorporated by reference, a family of genes is disclosed which are processed into peptides which, in turn, are expressed on cell surfaces, and can lead to lysis of the tumor cells by specific CTLs. These genes are referred to as the "MAGE" family, and are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes.

In U.S. patent application Ser. No. 938,334, the disclosure of which is incorporated by reference, nonapeptides are taught which bind to the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In a patent application Ser. No. 07/994,923 filed on Dec. 22, 1992 in the name of Boon-Falleur et al., entitled "Method For Identifying Individuals Suffering From a Cellular Abnormality, Some of Whose Abnormal Cells Present Complexes of HLA-A2/Tyrosinase Derived Peptides and Methods for Treating said Individuals", the complex of the title was identified as being implicated in certain cellular abnormalities. The application does not suggest, however, that any other HLA molecules might be involved in cellular abnormalities.

The prior presentation of MAGE-1 by an HLA-A1 molecule, as disclosed supra, also does not suggest that the protein can be presented by another HLA molecule. Thus, it is surprising that the very MAGE molecule presented by HLA-A1 has now been shown to be presented by HLA-C-clone 10. While the prior research is of value in understanding the phenomenon, it in no way prepares the skilled artisan for the disclosure which follows.

BRIEF DESCRIPTION OF THE FIGURE

FIG. 1 depicts experiments involving transfection of COS-7 with coding sequences for MAGE-1 and HLA-C-clone 10.

DETAILED DESCRIPTION OF PREFERRED EMBODIMENTS

Example 1

In the experiments which follow, various melanoma cell lines were used. These were obtained from melanoma patients identified as MZ2 and LB73. Cell lines MZ2-MEL.43, MZ2-MEL-3.0, and MZ2-MEL 3.1 are cloned sublines of MZ2-MEL, and are described in Van den Eynde et al., Int. J. Canc. 44: 634 (1989), as well as PCT patent application WO92/20356 (Nov. 26, 1992), both disclosures being incorporated by reference and in their entirety herewith. Cell line LB73-MEL was derived from patient LB73 in the same manner as the other cell lines described herein.

Samples containing mononuclear blood cells were taken from patient MZ2. A sample of the melanoma cell line MZ2-MEL.43 was irradiated, and then contacted to the mononuclear blood cell containing samples. The mixtures were observed for lysis of the melanoma cell lines, this lysis indicating that cytolytic T cells ("CTLs") specific for a complex of peptide and HLA molecule presented by the melanoma cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS, and incubated for 45 minutes at 37° C. with 200 μCi/ml of Na($^{51}$Cr)O$_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells were distributed into 96 well microplates. Samples of PBLs were added in 100 ul of the same medium, and assays were carried out in duplicate. Plates were centrifuged for 4 minutes at 100 g, and incubated for four hours at 37° C. in a 5.5% $CO_2$ atmosphere.

Plates were centrifuged again, and 100 ul aliquots of supernatant were collected and counted. Percentage of $^{51}Cr$ release was calculated as follows:

$$\%\ ^{51}Cr\ \text{release} = \frac{(ER - SR)}{(MR - SR)} \times 100$$

where ER is observed, experimental $^{51}Cr$ release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology.

These experiments led to the isolation of several CTL clones from patient MZ2 including CTL clone "81/12".

The experiment was repeated as described, using both cell line MZ2-MEL 3.0 and MZ2-MEL 3.1. The results indicated that clone 81/12 recognized both MZ2-MEL.43 and MZ2-MEL 3.0, but not MZ2-MEL 3.1. The antigen being recognized by 81/12 is referred to hereafter as "antigen Bb".

Example 2

In view of prior work, as summarized supra, it was of interest to determine the HLA class 1 profile for patient MZ2. This was determined following standard methodologies, which are now set forth. To obtain cDNA clones coding for the genes of the HLA class 1 molecules of the patients, a cDNA library was prepared, starting with total mRNA extracted from cell line MZ2-MEL.43, using well known techniques not repeated here. The library was inserted into plasmid pcD-SRα, and then screened, using an oligonucleotide probe containing a sequence common to all HLA class 1 genes, i.e.:

5'-ACTCCATGAGGTATTTC-3' (SEQ ID NO: 1)

One clone so identified was clone IC4A7 which, upon sequencing, was found to be functionally equivalent, if not identical to, HLA-C-clone 10, a well known human leukocyte antigen molecule. The sequence of the DNA coding for HLA-C clone 10 is taught by, e.g., Cianetti et al., Immunogenetics 29: 80–91 (1989), and the sequence is available under GENBANK accession number HUMMHCACA. An updated sequence is reported by Zemmour et al., Immunogenetics 37: 239–250 (1993), the disclosure of which is incorporated by reference in its entirety, as is Cianetti et al., supra. The Zemmour sequence is also available in the EMBL sequence bank.

Example 3

It was of interest to determine if the HLA molecule identified supra presented a mage derived tumor rejection antigen, and if the resulting complex of antigen and HLA molecule was recognized by a CTL clone of patient MZ2. To determine this, recipient cells were transfected with cDNA coding HLA-C clone 10, and with one of MAGE-1, MAGE-2, or MAGE-3 cDNA. The MAGE-1 cDNA was inserted into plasmid pcDNA I/Amp, while MAGE-2 and MAGE-3 cDNA were inserted into plasmid pcD-SRα.

Samples of recipient COS-7 cells were seeded, at 15,000 cells/well into tissue culture flat bottom microwells, in Dulbecc's modified Eagles Medium ("DMEM") supplemented with 10% fetal calf serum. The cells were incubated overnight at 37° C., medium was removed and then replaced by 30 µl/well of DMEM medium containing 10% Nu serum, 400 µg/ml DEAE-dextran, 100 µM chloroquine, and 100 ng of the subject plasmids (i.e., 100 ng of the IC4A7 clone, and 100 ng of the MAGE-cDNA plasmid). Following four hours of incubation at 37° C., the medium was removed, and replaced by 50 µl of PBS containing 10% DMSO. This medium was removed after two minutes and replaced by 200 µl of DMEM supplemented with 10% FCS.

Following this change in medium, COS cells were incubated for 48 hours at 37° C. Medium was then discarded, and 2000 cells of CTL clone 81/12 were added, in 100 µl of Iscove medium containing 10% pooled human serum. Supernatant was removed after 24 hours, and TNF content was determined in an assay on WEHI cells, as described by Traversari et al., Immunogenetics 35: 145–152 (1992), the disclosure of which is incorporated by reference.

The results, set forth in FIG. 1 demonstrate that a tumor rejection antigen, derived from MAGE-1, is presented by HLA-C-clone 10, and is recognized by CTL clone 81/12, whereas expression of MAGE-2 and MAGE-3 does not lead to presentation of the appropriate antigen.

The foregoing experiments demonstrate that HLA-C-clone 10 presents a MAGE-1 derived peptide as a tumor rejection antigen, leading to lysis of the presenting cells. There are ramifications of this finding, discussed infra. For example, CTL clone 81/12 is representative of CTLs specific for the complex in question. Administration of such CTLs to a subject is expected to be therapeutically useful when the patient presents HLA-C-clone 10 phenotype on abnormal cells. It is within the skill of the artisan to develop the necessary CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. It has been pointed out that the sequence for HLA-C is known to the art through GENBANK and EMBL, and the sequence for MAGE-1, together with a detailed protocol for its isolation, is provided by the PCT application and Van der Bruggen et al., both of which are incorporated by reference in their entirety, supra. COS cells, such as those used herein are widely available, as are other suitable host cells.

To detail the therapeutic methodology, referred to as adoptive transfer (Greenberg, J. Immunol. 136(5): 1917 (1986); Riddel et al., Science 257: 238 (Jul. 10, 1992); Lynch et al., Eur. J. Immunol. 21: 1403–1410 (1991); Kast et al., Cell 59: 603–614 (Nov. 17, 1989), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the HLA-C-clone 10/MAGE-1 derived peptide complex. This can be determined very easily. For example CTLs are identified using the transfectants discussed supra, and once isolated, can be used with a sample of a subject's abnormal cells to determine lysis in vitro. If lysis is observed, then the use of specific CTLs in such a therapy may alleviate the condition associated with the abnormal cells. A less involved methodology examines the abnormal cells for HLA-C clone 10, and of MAGE-1 expression via amplification using, e.g., PCR.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. U.S.A. 88: 110–114 (January, 1991) exemplify this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining MAGE-1 itself with an adjuvant to facilitate incorporation into HLA-C-clone 10 presenting cells. The protein is then processed to yield the peptide partner of the HLA molecule.

The foregoing discussion refers to "abnormal cells" and "cellular abnormalities". These terms are employed in their broadest interpretation, and refer to any situation where the cells in question exhibit at least one property which indicates that they differ from normal cells of their specific type. Examples of abnormal properties include morphological and biochemical changes, e.g. Cellular abnormalities include tumors, such as melanoma, autoimmune disorders, and so forth.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Method for determining cancer in a subject having malignant cells which present complexes of HLA-C clone 10 and MAGE-1 derived peptides on their surfaces, comprising contacting a CTL containing sample taken from a subject suspected of having cancer with cells which express both (i) molecules of HLA-C clone 10 and (ii) molecules of MAGE-1, and determining at least one of proliferation of cytolytic T cells in said CTL containing sample or lysis of said cells which express both (i) molecules of HLA-C clone 10 and (ii) molecules of a MAGE-1 gene to determine presence of cytolytic T cells which specifically bind complexes of HLA-C clone 10 and a MAGE-1 derived peptide as a determination that said subject has cancer.

2. The method of claim 1, wherein said cells which express both (i) molecules of HLA-C clone 10 and (ii) molecules of MAGE-1 are transfectants.

3. The method of claim 1, wherein said cells which express both (i) molecules of HLA-C clone 10 and (ii) molecules of MAGE-1 have been transfected with at least one of (i) a nucleic acid molecule which codes for HLA-C-clone 10 and (ii) a nucleic acid molecule which codes for tumor rejection antigen precursor MAGE-1.

4. The method of claim 1, wherein said cells which express both (i) molecules of HLA-C clone 10 and (ii)

molecules of MAGE-1 have been transfected with both (i) a nucleic acid molecule which codes for HLA-C-clone 10 and (ii) a nucleic acid molecule which codes for tumor rejection antigen precursor MAGE-1.

5. The method of claim 3, wherein said transfected cells are COS cells.

6. The method of claim 1, comprising determining proliferation of said cytolytic T cells via determining tumor necrosis factor release by said cytolytic T cells.

7. The method of claim 1, comprising determining lysis of said cells which express both (i) molecules of HLA-C clone 10 and (ii) molecules of MAGE-1 via a $^{51}Cr$ chromium release assay.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1:

ACTCCATGAG GTATTTC　　　　　　　　　　　　　　　　　　　　　　　　　　　　　　　　　　　　　　　17